(12) United States Patent
Horwitz

(10) Patent No.: US 6,447,765 B1
(45) Date of Patent: Sep. 10, 2002

(54) USE OF CYTOKINES AND MITOGENS TO INHIBIT GRAFT VERSUS HOST DISEASE

(75) Inventor: David A. Horwitz, Santa Monica, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/261,890

(22) Filed: Mar. 3, 1999

Related U.S. Application Data

(60) Provisional application No. 60/076,677, filed on Mar. 3, 1998.

(51) Int. Cl.$^7$ ............... A61K 45/00; A01N 65/00; A01N 63/00

(52) U.S. Cl. .............. 424/85.1; 424/93.7; 424/85.2; 424/93.71

(58) Field of Search ............... 514/2; 424/85.1, 424/85.2, 93.7, 93.71

(56) References Cited

FOREIGN PATENT DOCUMENTS

| WO | 93/17698 | | 9/1993 |
|----|----------|---|--------|
| WO | 97/42324 | | 11/1997 |
| WO | WO 9742324 | * | 11/1997 |
| WO | 99/25366 | | 5/1999 |
| WO | 00/66158 | | 11/2000 |

OTHER PUBLICATIONS

Rook et al. J Immunology 136:10, pp. 3916–3920 (1986).*
Murphy, W.J. et al. The potential role of NK cells in the separation of graft–versus–tumor effects from graft–versus–host disease after allogeneic bone marrow transplantation. Immunological Reviews. 1997. vol. 157, pp. 167–176.*
Martin, "Overview of Marrow Transplantation Immunology", in Bone Marrow Transplantation (eds. Forman et al.) pp. 16–21, Boston, *Blackwell Scientific Publications* (1994).
Dupont, B., "Immunology of hematopoietic stem cell transplantation: a brief review of its history", *Immunol Reviews* 157:5–12 (1997).
Rodt, H., "Anti–lymphocytic antibodies and marrow transplantation. 3. Effect of heterologous anti–brain antibodies on acute secondary disease in mice", *Eur. J. Immunol* 4:25–29 (1974).
Han et al., "A New Type of CD4+ Suppressor T cell Completely Prevents Spontaneous Autoimmune Diabetes and Recurrent Diabetes in Syngeneic Islet–Transplanted NOD Mice," *J Autoimmunity* 9:331–339 (1996).
Rook, et al., "Effects of Transforming Growth Factor β on the Functions of Natural Killer Cells: Depressed Cytolytic Activity and Blunting of Interferon Responsiveness," *J Immunology* 136:10:3916–3920 (1986).

Vallera et al., "Bone marrow transplantation across major histocompatibility barriers in mice. Effect of elimination of T cells from donor grafts by treatment with monoclonal Thy–1.2 plus complement or antibody alone", *Transplantation* 31:218–222 (1981).
Martin et al., "Effects of in vitro depletion of T cells in HLA–identical allogeneic marrow grafts", *Blood* 66:664–672 (1985).
Patterson et al., "Graft rejection following HLA matched T–lymphocyte depleted bone marrow transplantation", *Br J Haematol* 63:221–230 (1986).
Goldman et al., "Bone marrow transplantation for chronic myelogenous leukemia in chronic phase. Increased risk for relapse associated with T–cell depletion", *Ann Intern Med* 108:806–814 (1988).
Lucas et al., "The development of cellular immunity to Epstein–Barr virus after allogeneic bone marrow transplantation" , *Blood* 87:2594–2603 (1996).
Blazar et al., "FK506 inhibits graft–versus–host disease and bone marrow graft rejection in murine recipients of MHC disparate donor grafts by interfering with mature peripheral T cell expansion post–transplantation", *J. Immunol* 153:1836–1846 (1994).
Blazar et al., "Murine recipients of fully mismatched donor marrow are protected form lethal graft–versus–host disease by the in vivo administration of rapamycin but develop an autoimmune–like syndrome", *J. Immunol* 151:5726–5741 (1993).
Dumont et al., "Distinct Mechanisms of Suppression of Murine T Cell Activation by the Related macrolides FK–506 and Rapamycin", *J. Immunol* 144:251–258 (1990).
Morris, "Prevention and treatment of allograft rejection in vivo by rapamycin: molecular and cellular mechanisms of action", *Ann NY Acad Sci* 685:68–72 (1993).
Gratama et al., "Treatment of Acute Graft–Versus–Host Disease With Monoclonal Antibody OKT3. Clinical results and effect on circulating T lymphocytes", *Transplantation* 38(5):469–474 (1984).
Hiruma et al., "Effects of anti–CD3 monoclonal antibody on engraftment of T–cell–depleted bone marow allografts in mice: host T–cell suppression, growth factors, and space", *Blood* 79:3050–3058 (1992).
Anasetti et al., "Treatment of acute graft–versus–host disease with a nonmitogenic anti–CD3 monoclonal antibody", *Transplantation* 54:844–851 (1992).
Martin et al., "Effects of treating marrow with a CD3–specific immunotoxin for prevention of acute graft–versus–host disease", *Bone Marrow Transplant* 3:437–444 (1989).

(List continued on next page.)

Primary Examiner—Christina Y. Chan
Assistant Examiner—Maher Haddad
(74) Attorney, Agent, or Firm—Robin M. Silva; Renee M. Kosslak; Dorsey & Whitney LLP

(57) ABSTRACT

The field of the invention is generally related to pharmaceutical agents useful in treating graft-versus-host disease (GVHD) in patients that have received allogenic bone marrow transplants.

4 Claims, 4 Drawing Sheets

OTHER PUBLICATIONS

Herve et al., "Treatment of Corticosteroid Resistant Acute Graft–Versus–Host Disease by In Vivo Administration of Anti–Interleukin–2 Receptor Monoclonal Antibody (B–B10)", *Blood* 75(4):1017–1023 (1990).

Boussiotis et al., "B7 but not intercellular adhesion molecule–1 costimulation prevents the induction of human alloantigen–specif tolerance," *J Exp Med* 178:1753–1763 (1993).

Gribben et al., "Complete blockade of B7 family–mediated costimulation is necessary to induce human alloantigen–specific anergy: a method to ameliorate graft–versus–host disease and extend the donor pool", *Blood* 97:4887–4893 (1996).

Blazar et al., "Recent advances in graft–versus–host disease (GVHD)", *Immunol Rev* 157:79–90 (1997).

Krenger et al., "Effects of exogenous interleukin–10 in a murine model of graft–versus–host disease to minor histocompatibility antigens", *Transplantation* 58:1251–1257 (1994).

Blazar et al., Both CD4+ and CD8+ T Cells Can Cause Accelerated GVHD Lethality in the Presence of High In Vivo Doses of Exogenous Ill10: Role of Interfereon Gamma (IFNγ) in GVHD Induction, *Blood* 88:247 (1996) (abstract).

Krenger et al., "Polarized type 2 alloreactive CD4+ and CD8+ donor T cells fail to induce experimental acute graft–versus–host disease", *J Immunol* 153:585–593 (1995).

Fowler et al., "Donor CD4–enriched cells of Th2 cytokine phenotype regulate graft–versus–host disease without impairing allogeneic engraftment in sublethally irradiated mice", *Blood* 84:3540–3549 (1994).

Bonini et al., HSY–TK gene transfer into donor lymphocytes for control of allogeneic graft–versus–leukemia, *Science* 276:1719–1724 (1997).

Storb et al., "Long–term follow–up of a controlled trial comparing a combination of methotrexate plus cyclosporine with cyclosporine alone for prophylaxis of graft–versus–host disease in patients administered HLA–identical marrow grafts for leukemia", *Blood* 80:560–561 (1992).

Sullivan et al., "Chronic Graft–Versus–Host Disease and Other Late Complications of Bone Marrow Transplantation", *Semin Hematol* 28:250–259 (1992).

Via et al., "Critical Role of interleukin–2 in the development of acute graft–versus–host disease", *International Immunol* 5:565–572 (1993).

Fast, "Generation and characterization of IL–2 activated veto cells", *J Immunol* 149:1510–1515 (1992).

Hirohata et al., "Role of II–2 in the generation of CD4+ suppressors of human B cell responsiveness", *J Immunol* 142:3104–3112 (1989).

Taylor, "Antigen specific suppressor T cells respond to cytokines released by T cells", *Advances Exp Med Biol* 319:125–135 (1992).

Kinter et al., "Interleukin 2 induces CD8+ T cell–mediated suppression of human immunodeficiency virus replication in CD4+ T cells and this effect overrides its ability to sitmulate virus expression", *Proc. Natl. Acad. Sci, USA* 92:10985–10989 (1995).

Barker et al., "Identification of multiple and distinct CD8+ T cell suppressor activities: dichotomy between infected and uninfected individuals, evolution with progression of disease, and sensitivity to gamma irradiation," *J Immunol* 156:4476–4483 (1996).

Hirokawa et al., "Human resting B lymphocytes can serve as accessory cells for anti–CD2–induced T cell activation", *J. Immunol.* 149:1859–1866, 1992.

Gray et al., "The role of transforming growth factor beta in the generation of suppression: an interaction between CD8+ T and NK cells", *J Exp Med* 180:1937–1942 (1994).

Gray et al., "Generation of an Inhibitory Circuit Involving CD8+ T Cells, IL–2 and NK Cell–Derived TGF–β: Contrasting Effects of Anti–CD2 and Anti–CD3", *J Immunol*, 160:2248–2254 (1998).

Border et al., "Transforming growth factor–beta in disease: the dark side of tissue repair," *J Clin Invest* 90:1–7 (1992).

Sporn et al., "Some recent advances in the chemistry and biology of transforming growth factor–beta, " *J Cell Biol* 105:1039–1045 (1987).

Massague, "Receptors for the TGF–bata family", *Cell* 69:1067–1070 (1992).

Murphy et al, "The potential role of NK cells in the separation of graft–versus–tumor effects from graft–versus–host disease after allogeneic bone marrow transplantation," *Immunol Rev* 157:167–176 (1997).

Chavin, et al., "Anti–CD2 mAbs Suppress Cytotoxic Lymphocyte Activity by the Generation of Th2 Suppressor Cells and Receptor Blockade," *J Immunol* 152:3729–3739 (1994).

Asai O, et al., "Suppression of graft–versus–host disease and amplification of graft–versus–tumor effects by activated natural killer cells after allogeneic bone marrow transplantation," *Journal of Clinical Investigation* 101(9):1835–1842 (1998).

Zehavi–Willner et al., "The Mitogenic Activity of Staphylococcal Enterotixin B (SEB): A Monovalent T Cell Mitogen That Stimulates Cytoloytic T Lymphocytes but Cannot Mediate Their Lytic Interaction," *Journal of Immunology* 127(8):2682–2687 (1986).

Pawelec, et al., "Cytokine Modulation of TH1/Th2 Phenotype Differentiation in Directly Alloresponsive CD4+ Human T Cells," Transplantation, 62(8):1095–1101 (Oct. 1996).

Halverson, et al., "In Vitro Generation of Allospecific Human CD8+ T Cells of Tc1 and Tc2 Phenotype," Blood, 90(5):2089–2096 (Sep. 1997).

Zeller, et al., "Ex vivo IL10 and TGF–Beta Act Synergistically to Induce CD4+ Alloantigen–Specific Tolerance Resulting in Diminished Graft–Versus–Host Disease in Vivo," FASEB Journal, (Mar. 12, 1999) 13(4)part 1, A614. Meeting Info: Annual Meeting of the Professional Research Scientists for Experimental Biology. Apr. 17–21, 1999.

Oswald, et al., "Il–10 Synergizes with IL–4 and Transforming Growth Factor–Beta to Inhibit Macrophage Cytotoxic Activity," Journal of Immunology, 148(11):3578–3582 (1992).

* cited by examiner

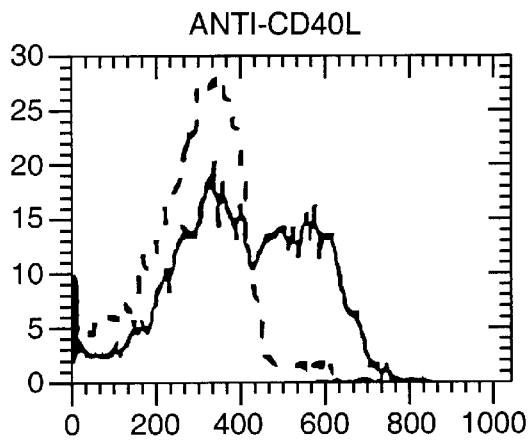
FIG._1A
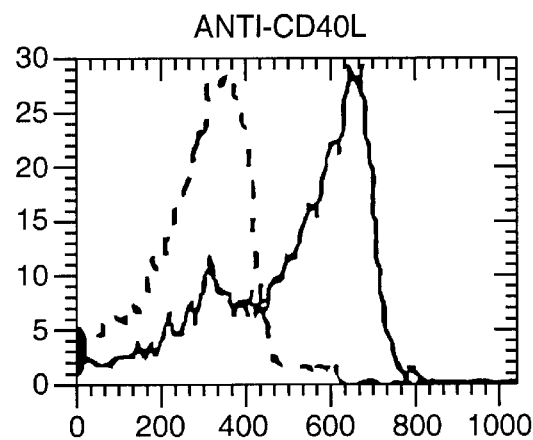
FIG._1B
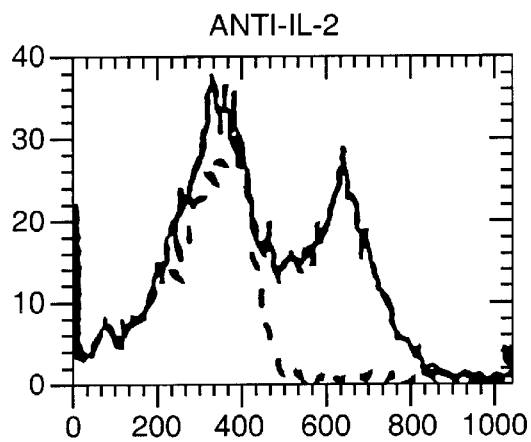
FIG._3A
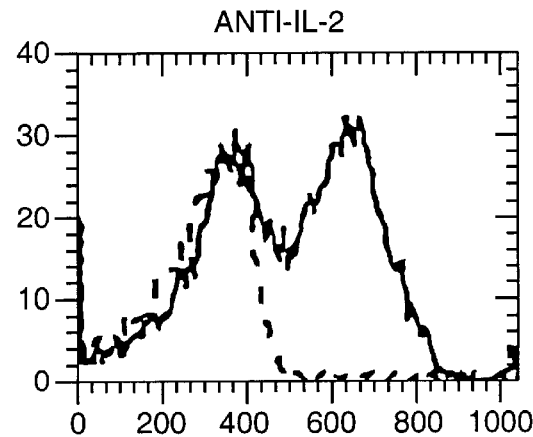
FIG._3B

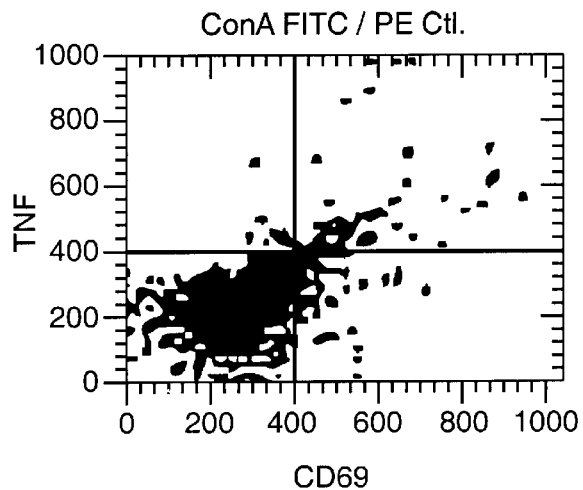
FIG._2A
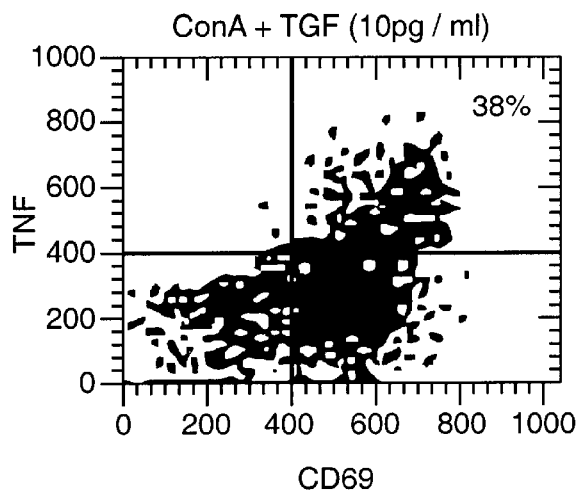
FIG._2B
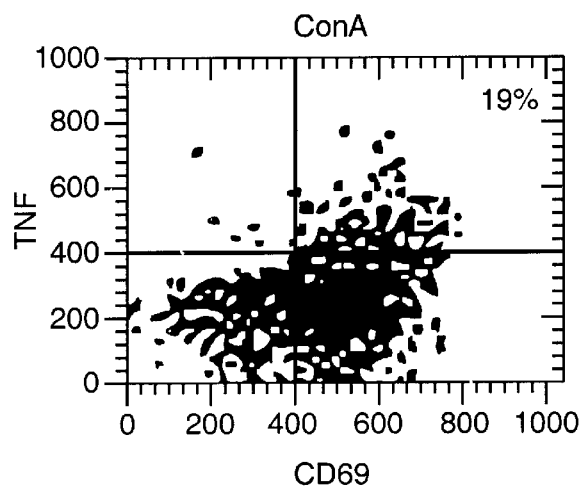
FIG._2C
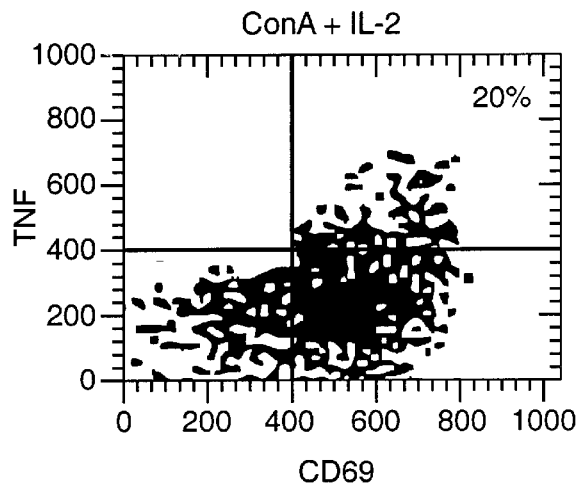
FIG._2D

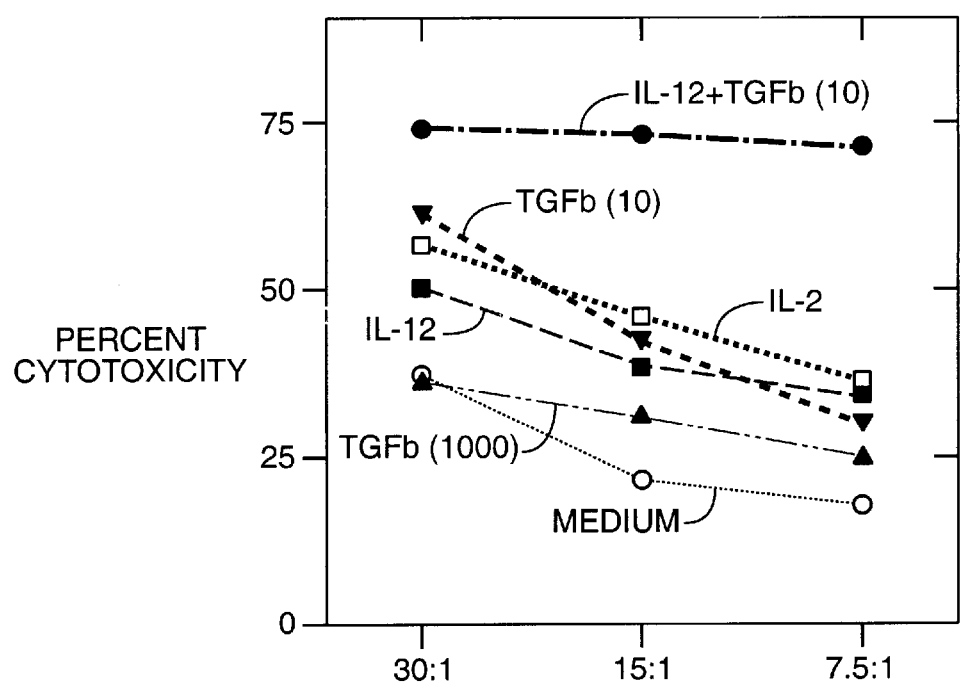
FIG._4A
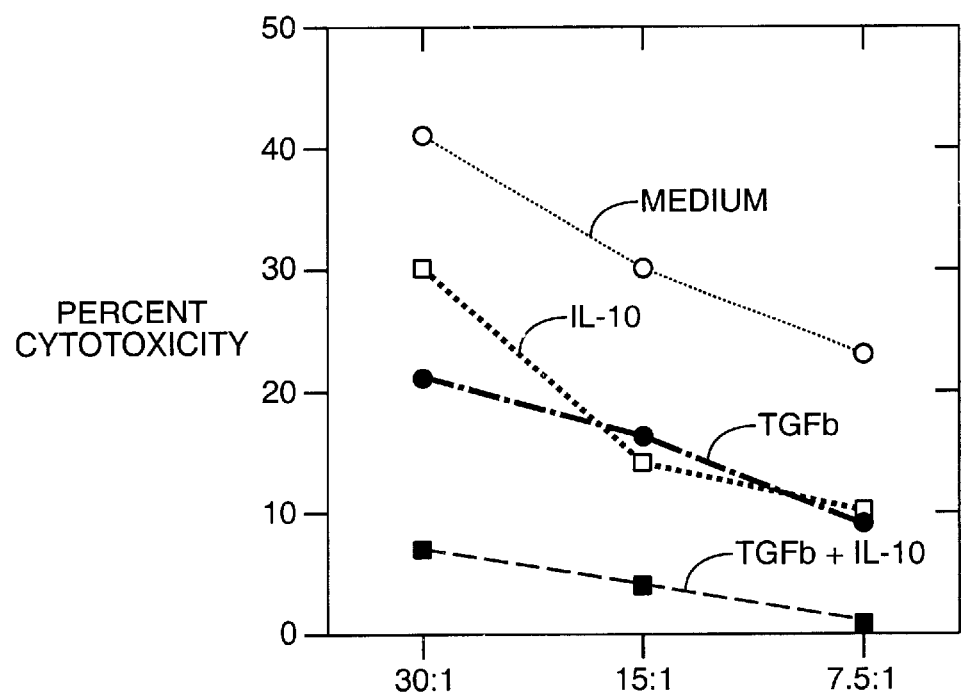
FIG._4B

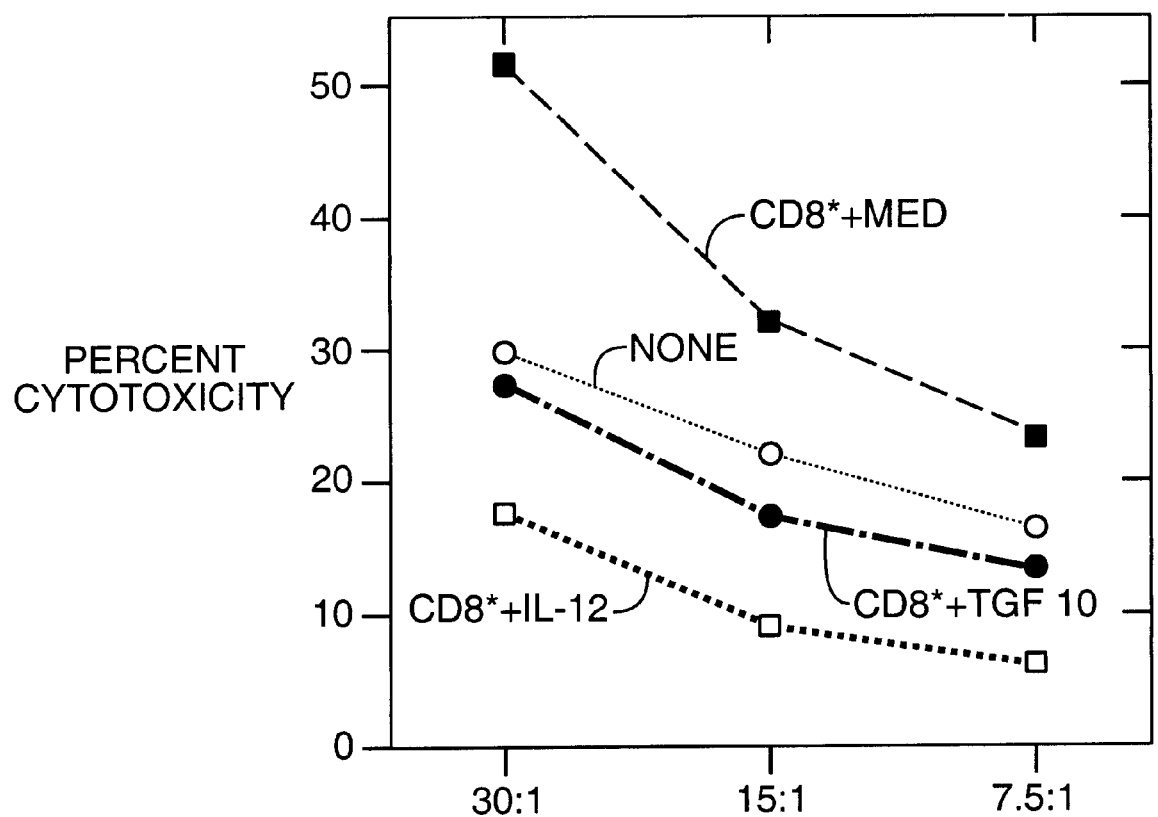
FIG._4C

USE OF CYTOKINES AND MITOGENS TO INHIBIT GRAFT VERSUS HOST DISEASE

This application claims the benefit of U.S. Ser. No. 60/076,677, filed Mar. 3, 1998.

FIELD OF THE INVENTION

The field of the invention is generally related to pharmaceutical agents useful in treating graft-versus-host disease (GVHD) in patients that have received allogenic bone marrow transplants.

BACKGROUND OF THE INVENTION

Organ transplantation is now used with great success to improve the quality of human life. Substantial progress has been made in using kidneys, hearts, and livers from unrelated individuals. However, transplantation of hematopoietic stem cells from an unrelated (or allogeneic) donor is a more complicated endeavor. Here multipotent stem cells which have the capacity to regenerate all the blood-forming elements and the immune system are harvested from bone marrow or peripheral blood from one individual are transferred to another. However, histocompatibility differences between donor and recipient results in a higher incidence of transplant-related complications, and has limited the use of this procedure (Forman et al., *Blackwell Scientific Publications*, 1994).

It is unfortunate that only few individuals are candidates for allogeneic hematopoietic stem cell transplantation at the present time because the spectrum of diseases treatable by this procedure has steadily increased. These diseases now include hematologic malignancies such as the acute or chronic leukemias, multiple myeloma, myelodysplastic syndromes; lymphomas; and the severe anemias such as aplastic anemia or thalassemia.

Allogeneic stem cell transplantation begins with treatment of the recipient with a highly immunosuppressive conditioning regimen. This is most commonly accomplished with high doses of chemotherapy and radiation which effectively kill all the blood forming elements of the bone marrow. Besides preparing the recipient bone marrow for donor stem cell transplantation, the conditioning regimen serves to kill much of the malignancy that remains in the body. The period of time between the completion of the conditioning regimen, and engraftment of the donor stem cells is the most dangerous for the recipient. It is during this time that the patient is completely immunocompromised and susceptible to a host of life-threatening infections. This vulnerability persists until the grafted donor stem cells proliferate and differentiate into the needed white blood cells and immune cells needed to combat infections.

Moreover, donor stem cell preparations generally contain immune cells called T lymphocytes. Unless the donor stem cells originate from an identical twin the transferred T cells turn against the recipient's tissues and trigger a deadly ailment called graft versus host disease (or GVHD). This is because the donor T lymphocytes recognize histocompatibility antigens of the recipient as foreign and respond by causing multi-organ dysfunction and destruction.

Current techniques of immunosuppression have made allogeneic stem cell transplantation from a related, histocompatible (HLA-matched) donor much safer than it once was. Allogeneic stem cell transplantation from an unrelated, HLA-matched donor is commonly complicated by serious, often fatal GVHD. The threat of GVHD is even higher when the stem cell donor is HLA mismatched.

Since only 30% of patients in need of allogeneic stem cells will have a sibling with identical histocompatibility antigens (Dupont, B., *Immunol Reviews* 157:12, 1997), there is a great need to make HLA-matched unrelated, and HLA-mismatched transplantation a safer procedure. There have been two principal approaches to resolving this problem. The first has been to deplete the graft of contaminating T lymphocytes and the second has been to inactivate the T cells so they cannot attack the recipient.

In the 1970's it became evident that ex-vivo removal of mature T lymphocytes from a bone marrow graft prior to transplantation dramatically decreased or prevented GVHD in animals receiving marrow grafts across major histocompatibility barriers (Rodt, H. *J. Immunol* 4:25–29, 1974; and 4 Vallera et al., *Transplantation* 31:218–222, 1981). However, with T cell depletion the incidence of graft failure, graft rejection, relapse of leukemia, and viral-induced lympho-proliferative disease markedly increased (Martin et al. *Blood* 66:664–672, 1985; 6 Patterson et al. *Br J Hematol* 63:221–230, 1986; Goldman et al. *Ann Intem Med* 108:806–814, 1988; and Lucas et al. *Blood* 87:2594–2603, 1996). Thus, the transplantation of donor T cells on the stem cells has beneficial as well as deleterious effects. One needs the facilitating effect of the T cells on the engraftment of stem cells and the now well recognized graft-versus-tumor effects, but not graft-versus host disease.

Several approaches have been used to decrease T cell activation. These include: 1) in vivo immunosuppressive effects of drugs such as FK506 and rapamycin (Blazar et al. *J. Immunol* 153:1836–1846, 1994; Dupont et al. *J. Immunol* 144:251–258, 1990; Morris, *Ann NY Acad Sci* 685:68–72. 1993; and Blazar et al. *J Immunol* 151:5726–5741, 1993); 2) the in vivo targeting of GVHD-reactive T cells using intact and F(ab')2 fragments of monoclonal antibodies(mAb) reactive against T cell determinants or mAb linked to toxins (Gratama et al. *Amj Kidney Dis* 11:149–152, 1984; Hiruma et al. *Blood* 79:3050–3058, 1992; Anasetti et al. *Transplantation* 54:844–851, 1992; Martin et al. *Bone Marrow Transplant* 3:437–444, 1989); 3) inhibition of T cell signaling via either IL-2/cytokine receptor interactions (Herve et al. *Blood* 76:2639–2640, 1990) or the inhibition of T cell activation through blockade of co-stimulatory or adhesogenic signals (Boussiotis et al. *J Exp Med* 178:1753–1763, 1993; Gribben et al. *Blood* 97:4887–4893, 1996; and Blazar et al. *Immunol Rev* 157:79–90, 1997); 4) the shifting of the balance between acute GVHD-inducing T helper-type 1 T cells to anti-inflammatory T helper-type 2 T cells via the cytokine milieu in which these cells are generated (Krenger et al. *Transplantation* 58:1251–1257, 1994; Blazar et al. *Blood* 88:247, 1996, abstract; Krenger et al. *J Immunol* 153:585–593. 1995; Fowler et al. *Blood* 84:3540–3549, 1994); 5) the regulation of alloreactive T cell activation by treatment with peptide analogs which affect either T cell receptor/major histocompatibility complex (MHC) interactions, class II MHC/CD4 interactions, or class I MHC/CD8 interactions (Townsend and Korngold (unpublished data)); and 6) the use of gene therapy to halt the attack of donated cells on the recipient's tissues (Bonini et al. *Science* 276:1719–24, 1997).

There is suggestive evidence that the T lymphocytes from non-identical donors can become tolerant to the recipient's tissues. Unlike patients who receive solid organ allografts for whom life-long immunosuppressive therapy is needed to control chronic rejection, there is evidence of immunologic tolerance with stem cell allografts. The majority of these patients can be withdrawn from immune suppression without further evidence of GVHD (Storb et al. *Blood*

80:560–561, 1992; and Sullivan et al. *Semin Hematol* 28:250–259, 1992).

Immunologic tolerance is a specific state of non-responsiveness to an antigen. Immunologic tolerance generally involves more than the absence of an immune response; this state is an adaptive response of the immune system, one meeting the criteria of antigen specificity and memory that are the hallmarks of any immune response. Tolerance develops more easily in fetal and neonatal animals than in adults, suggesting that immature T and B cells are more susceptible to the induction of tolerance. Moreover, studies have suggested that T cells and B cells differ in their susceptibility to tolerance induction. Induction of tolerance, generally, can be by clonal deletion or clonal anergy. In clonal deletion, immature lymphocytes are eliminated during maturation. In clonal anergy, mature lymphocytes present in the peripheral lymphoid organs become functionally inactivated.

Following antigenic challenge stimulation, T cells generally are stimulated to either promote antibody production or cell-mediated immunity. However, they can also be stimulated to inhibit these immune responses instead. T cells with these down-regulatory properties are called "suppressor cells".

Although it is known that T suppressor cells produce cytokines such as transforming growth factor beta (TGF-beta), interleukin 4 (IL-4) or interleukin (IL-10) with immunosuppressive effects, until recently the mechanisms responsible for the generation of these regulatory cells have been poorly understood. It was generally believed that CD4+ T cells induce CD8– T cells to develop down-regulatory activity and that interleukin 2 (IL-2) produced by CD4+ cells mediates this effect. Although most immunologists agree that IL-2 has an important role in the development of T suppressor cells, whether this cytokine works directly or indirectly is controversial (Via et al. *International Immunol* 5:565–572, 1993; Fast, *J Immunol* 149:1510–1515, 1992; Hirohata et al. *J Immunol* 142:3104–3112, 1989; Taylor, *Advances Exp Med Biol* 319:125–135, 1992; and Kinter et al., *Proc. Nati. Acad. Sci. USA* 92:10985–10989,1995). Recently, IL-2 has been shown to induce CD8+ cells to suppress HIV replication in CD4–T cells by a non-lytic mechanism. This effect is cytokine mediated, but the specific cytokine with this effect has not been identified (Barker et al. *J Immunol* 156:4476–83, 1996; and Kinter et al. *Proc Nat Acad Sci USA* 99:10985–9 1995).

A model using human peripheral blood lymphocytes to study T cell/B cell interactions in the absence of other accessory cells has been developed (Hirokawa et al. *J. Immunol.* 149:1859–1866, 19??). With this model it was found that CD4+ T cells by themselves generally lacked the capacity to induce CD8+ T cells to become potent suppressor cells. The combination of CD8+ T cells and NK cells, however, induced strong suppressive activity (Gray et al. *J Exp Med* 180:1937–1942, 1994). It was then demonstrated that the contribution of NK cells was to produce TGF-beta in its active form. It was then reported that a small non-immunosuppressive concentration (10–100 pg/ml) of this cytokine served as a co-factor for the generation of strong suppressive effects on IgG and IgM production (Gray et al. *J Exp Med* 180:1937–1942, 1994). Further, it was demonstrated that NK cells are the principal lymphocyte source of TGF-beta (Gray et al. *J Immunol,* 160:2248–2254, 1998).

TGF-beta is a multifunctional family of cytokines important in tissue repair, inflammation and immunoregulation (Border et al. *J Clin Invest* 90:1–7, 1992; and Sporn et al. *J Cell Biol* 105:1039–1045, 1987). TGF-beta is unlike most other cytokines in that the protein released is biologically inactive and unable to bind to specific receptors (Massague, *Cell* 69:1067–1070, 1992). The conversion of latent to active TGF-beta is the critical step which determines the biological effects of this cytokine.

There is some evidence that NK cell-derived TGF-beta has a role in the prevention of GVHD. Whereas the transfer of stem cells from one strain of mice to another histocompatibility mismatched strain resulted in death of all recipients from GVHD within 19 days, the simultaneous transfer of NK cells from the donor animals completely prevented this consequence. All the recipient mice survived indefinitely. This therapeutic effect, however, was completely blocked by antagonizing the effects of TGF-beta by the administration of a neutralizing antibody (Murphy et al. *Immunol Rev* 157:167-176, 1997).

It is very likely, therefore, that the mechanism whereby NK cell-derived TGF-beta prevented GVHD is similar to that described by Horwitz et al. in the down-regulation of antibody production. In each case NK cell-derived TGF-beta was responsible for the generation of suppressor lymphocytes that blocked these respective immune responses. The mouse study is of particular interest since the histocompatibility differences between genetically disparate inbred mice strains would mirror that of unrelated human donors. A modification of this strategy, therefore might overcome GVHD in mismatched humans.

Anti-CD2 monoclonal antibodies and other constructs that bind to the CD2 co-receptor have been shown to be immunosupressive. It has now been demonstrated that at least one mechanism to explain this immunosuppressive effect is by inducing the production of TGF-beta (Gray et al. *J Immunol,* 160:2248–2254, 1998).

One strategy to prevent GVHD would be to isolate and transfer NK cells along with the stem cells. Another would be to treat the immunocompromised recipient who has received allogeneic stem cells with TGF-beta, anti-CD2 monoclonal antibodies, IL-2 or a combination of these cytokines. The first strategy would be difficult because NK cells comprise only 10 to 20% of total lymphocytes so that it would be difficult to harvest a sufficient number of cells for transfer. The second strategy is limited by numerous effects on different body tissues and are not very safe to deliver to a patient systemically. What is needed, therefore, is a way to induce mammalian cells to suppress the development of GVHD ex vivo.

SUMMARY OF THE INVENTION

In accordance with the objects outlined above, the present invention provides methods for inducing T cell tolerance in a sample of ex vivo peripheral blood mononuclear cells (PBMCs) comprising adding a suppressive composition to the cells. The suppressive composition can be IL-10, TGF-β, or a mixture.

In an additional aspect, the present invention provides methods for treating donor cells to ameliorate graft versus host disease in a recipient patient. The methods comprise removing peripheral blood mononuclear cells (PBMC) from a donor, and treating the cells with a suppressive composition for a time sufficient to induce T cell tolerance. The cells are then introducing to a recipient patient. The PBMCs can be enriched for CD8+ cells, if desired. The methods may additionally comprising adding the treated cells to donor stem cells prior to introduction into the patient.

In an additional aspect, the invention provides kits for the treatment of donor cells comprising a cell treatment container adapted to receive cells from a donor and at least one dose of a suppressive composition. The kits may additionally comprising written instructions and reagents. The cell treatment container may comprise a sampling port to enable the removal of a fraction of the cells for analysis, and an exit port adapted to enable transport at least a portion of the cells to a recipient patient.

BRIEF DESCRIPTION OF THE DRAWINGS

FIGS. 1A and 1B depict that TGF-β can upregulate expression of CD40 Ligand (CD40L) on T cells. Purified T cells were stimulated with PMA (20 ng/ml) and ionomycin (5 μM) in the presence or absence of TGF-β. After 6 hours the cells were stained with anti-CD40L antibodies. In the absence of TGF-β, there were 30% positive cells (solid line, panel A). With 100 pg/ml of TGF-β, 66% of the cells were positive (solid line, panel B). The dotted line in both panenis is the reactivity of a control antibody.

FIGS. 2A, 2B, 2C and 2D depict that TGF-β increases TNF-α expression by CD8+ cells. Purified CD8+ cells were stimulated for 24 hours with Con A (5 pg/ml) + TGF-β (10 pg/ml)+ IL-2 (10 U). During the last 6 hours, monensin (2 μM) was also present to prevent cytokine release. The cells were first stained with anti-CD69 to distinguish the activated cells. Then the cells were fixed (4% paraformaldhyde), permeabilized (0.1% saponin) and stained with anti-TNF-α antibodies.

FIGS. 3A and 3B depict TGF-β, enhances IL-2 expression by T cells. Purified T cells were stimulated in the presence or absence of TGF-β (1 ng/ml). In the absence of TGF-β, 36% of the cells were positive (panel A, solid line) whereas with TGF-β, 53% were positive (panel B, solid line).

FIGS. 4A, 4B and 4C depict that TGF-β can enhance or inhibit cytotoxic activity. In panels A and B, purified T cells were cultured with irradiated allogenic stimulator cells in the presence or absence of the indicated cytokines. After 48 hours, the cells were washed and after a further 3 days, assayed for cytotoxic activity against $^{31}$Cr-labelled stimulator ConA blasts. In panel C, purified CD8+ cells were cultured with irradiated allogenic cells in the presence or absence of TGF-β(10 pg/ml) or IL-12 (100 U). After 48 hours, the cells were washed and added to autologous T cells and irradiated allogenic cells. After 5 days of culture, cytotoxic activity was determined using $^{31}$Cr-labelled stimulator ConA blasts as target cells.

DETAILED DESCRIPTION OF THE INVENTION

The present invention allows for the transfer of histoincompatible stem cells to humans with a variety of malignant or hereditary diseases using a method to prevent life-threatening graft-versus-host disease. This is accomplished by treatment of donor cells with a combination of mitogens and cytokines ex-vivo. The particular advantage of this procedure is that it avoids the removal of donor T cells which facilitate stem cell engraftment and that have the potential to attack any remaining malignant cells. Once a state of tolerance between donor and host has been achieved, non-conditioned donor T cells can be transferred to maximize the beneficial graft-versus-tumor immune response.

This strategy is unlike almost all other treatment modalities currently in use. These cytokines and mitogens described would have severe toxic side effects if administered in vivo. The ex-vivo protocol described avoids these side effects. The ability to successfully engraft histoincompatible stem cells for treatment of life-threatening diseases would be a milestone in medicine.

In addition, a further advantage of the present invention is that it may avoid or minimize the very toxic immunosuppressive medicines that must be given to the recipient to prevent GVHD. These medicines also block the ability of the donor-derived lymphocytes which repopulate the immune system of the recipient from becoming "educated" to their new host. Therefore, it is difficult to stop the immunosuppressive drugs, unless an alternative treatment such as the present invention is used.

The strategy of the present invention is to suppress GVHD by both suppressing T cell activation and inducing a tolerant state in the donor cells, which prevents the donor cells from attacking recipient cells. Surprisingly, the methods outlined herein result in not only the suppression of the treated cells but additionally induces them to prevent other donor cells from killing recipient cells as well, i.e. they become tolerant. That is, the methods outlined herein not only decrease the capacity of the donor's cells to attack the recipient's cells, but induces some of the donor's cells to assume a surveillance role and prevent other donor cells from mounting an immune attack against the recipient host. The net result is for the donor lymphocytes to be tolerant to the histocompatibility antigens of the recipient, but does not impair the ability of the new lymphocytes to attack tumor cells.

Another significant potential advantage of this strategy is a low probability of serious adverse side effects. Since only trace amounts of suppressive compositions such as cytokines will be returned to the patient, there should be minimal toxicity.

Accordingly, the present invention is drawn to methods of treating donor cells for transplantation into a recipient that comprise removing peripheral blood mononuclear cells (PBMCs) from the donor and treating the cells with a composition that is on one hand suppressive, but on the other hand generates surveillance cells to prevent an immune attack.

The present invention shows that the treatment of the donor cells by a suppressive composition blocks an immune attack against the recipient's cells. Without being bound by theory, it appears that there are several ways the methods of the invention may work. First of all, the donor cells are activated to become tolerant to the recipient's cells. Secondly, the donor CD8+ cells get activated to become regulatory cells, to prevent other donor cells from killing recipient cells. These results lead to amelioration of a GVH response. Without being bound by theory, it appears that the inhibition of cytotoxic activity may occur as a result of the effects TGF-β on the cells; as depicted in the figures, the addition of TGF-β causes the upregulation of CD40L on T cells, increases TNF-α expression by CD8+ cells, and enhances IL-2 expression.

Thus, in a preferred embodiment, the present invention induces tolerance in the donor cells to recipient tissue, thus avoiding GVHD, by treating them with a suppressive composition ex vivo.

Accordingly, the present invention provides methods of treating donor cells to induce or establish tolerance to recipient cells prior to transplantation into a recipient patient to decrease or eliminate a graft-versus-host response. By "T cell tolerance" herein is meant immune non-responsiveness to the recipient, i.e. a tolerance to the histocompatibility antigens of the recipient. Without being bound by theory, this may be due to anergy or death of the T cells. Preferably, the T cells retain the ability to recognize other antigens as foreign, to facilitate tumor killing and general immunological responses to foreign antigens.

Using the methods outlined herein, a GVH response is suppressed or treated. By "treating" GVHD herein is meant that at least one symptom of the GVHD is ameliorated by the methods outlined herein. This may be evaluated in a number of ways, including both objective and subjective factors on the part of the patient as is known in the art. For example, GVHD generally exhibits a skin rash, an abnormality in liver function studies, fever, general symptoms including fatigue, anemia, etc.

By "patient" herein is meant a mammalian subject to be treated, with human patients being preferred. In some cases, the methods of the invention find use in experimental animals and in the development of animal models for disease, including, but not limited to, rodents including mice, rats, and hamsters; and primates.

The methods provide for the removal of blood cells from a patient. In general, peripheral blood mononuclear cells (PBMCs) are taken from a patient using standard techniques. By "peripheral blood mononuclear cells" or "PBMCs" herein is meant lymphocytes (including T-cells, B-cells, NK cells, etc.) and monocytes. As outlined more fully below, it appears that the main effect of the suppressive composition is to enable CD8+ T cells to become tolerant. Accordingly, the PBMC population should comprise CD8+ T cells. Preferably, only PBMCs are taken, either leaving or returning red blood cells and polymorphonuclear leudocytes to the patient. This is done as is known in the art, for example using leukophoresis techniques. In general, a 5 to 7 liter leukophoresis step is done, which essentially removes PBMCs from a patient, returning the remaining blood components. Collection of the cell sample is preferably done in the presence of an anticoagulant such as heparin, as is known in the art.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer.

The PBMCs are generally concentrated for treatment, using standard techniques in the art. In a preferred embodiment, the leukophoresis collection step results a concentrated sample of PBMCs, in a sterile leukopak, that may contain reagents or doses of the suppressive composition, as is more fully outlined below. Generally, an additional concentration/purification step is done, such as FicollHypaque density gradient centrifugation as is known in the art.

In a preferred embodiment, the PBMCs are then washed to remove serum proteins and soluble blood components, such as autoantibodies, inhibitors, etc., using techniques well known in the art. Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors of TGF-β) although buffers such as Hanks balanced salt solution (HBBS) or physiological buffered saline (PBS) can also be used.

Generally, the cells are then counted; in general from $1 \times 10^9$ to $2 \times 10^9$ white blood cells are collected from a 5–7 liter leukophoresis step. These cells are brought up roughly 200 mls of buffer or media.

In a preferred embodiment, the PBMCs may be enriched for one or more cell types. For example, the PBMCs may be enriched for CD8+ T cells, CD4+ T cells or, in the case of stem cell isolation as is more fully described below, CD34+ stem cells. This is done as is known in the art, as described in Gray et al. (1998), *J. Immunol.* 160:2248, hereby incorporated by reference. Generally, this is done using commercially available immunoabsorbent columns, or using research procedures (the PBMCs are added to a nylon wool column and the eluted, nonadherent cells are treated with antibodies to CD4, CD16, CD11b, and CD74, followed by treatment with immunomagnetic beads, leaving a population enriched for CD8+ T cells). In one embodiment, cell populations are enriched for CD8+ cells, as these appear to be the cells most useful in the methods of the invention. However, one advantage of using PBMCs is that other cell types within the PBMC population produce IL-10, thus decreasing or even eliminating the requirement of the suppressive composition comprising IL-10.

Once the cells have undergone any necessary pretreatment, the cells are treated with a suppressive composition. By "treated" in this context herein is meant that the cells are incubated with the suppressive composition for a time period sufficient to result in T cell tolerance, particularly when transplanted into the recipient patient. The incubation will generally be under physiological temperature.

By "suppressive composition" or "tolerance composition" is meant a composition that can induce T cell tolerance. Generally, these compositions are cytokines. Suitable suppressive compositions include, but are not limited to, IL-10, IL-2 and TGF-β. A preferred suppressive composition is a mixture of IL-10 and TGF-β.

The concentration of the suppressive composition will vary on the identity of the composition, but will generally be at physiologic concentration, i.e. the concentration required to give the desired effect, i.e. an enhancement of specific types of regulatory cells. In a preferred embodiment, TFG-β is used in the suppressive composition. By "transforming growth factor -β" or "TGF-β" herein is meant any one of the family of the TGF-βs, including the three isoforms TGF-β1, TGF-β2, and TGF-β3; see Massague, (1980), *J. Ann. Rev. Cell Biol* 6:597. Lymphocytes and monocytes produce the β1 isoform of this cytokine (Kehrl et al. (1991), *Int J Cell Cloning* 9:438–450). The TFG-0 can be any form of TFG-β that is active on the mammalian cells being treated. In humans, recombinant TFG-β is currently preferred. A human TGF-β2 can be purchased from Genzyme Pharmaceuticals, Farmington, Mass. In general, the concentration of TGF-β used ranges from about 2 picograms/ml of cell suspension to about 2 nanograms, with from about 10 pg to about 500 pg being preferred, and from about 50 pg to about 150 pg being especially preferred, and 100 pg being ideal.

In a preferred embodiment, IL-10 is used in the suppressive composition. The IL-10 can be any form of IL-10 that is active on the mammalian cells being treated. In humans, recombinant IL-10 is currently preferred. Recombinant human IL-10 can be purchased. In general, the concentration of IL-10 used ranges from about 1 U/ml of cell suspension to about 100, with from about 5 to about 50 being preferred, and with 10 U/ml being especially preferred.

In a preferred embodiment, IL-2 is used as the suppressive composition. The IL-2 can be any form of IL-2 that is active on the mammalian cells being treated. In humans, recombinant IL-2 is currently preferred. Recombinant human IL-2 can be purchased from Cetus, Emeryville, Calif. In general, the concentration of IL-2 used ranges from about 1 Unit/ml of cell suspension to about 100 U/ml, with from about 5 U/ml to about 25 U/ml being preferred, and with 10 U/ml being especially preferred. In a preferred embodiment, IL-2 is not used alone.

In a preferred embodiment, TGF-β can be used alone as the suppressive composition. Alternate preferred embodiments utilize IL-10 alone, combinations of TGF-β, IL-10 and IL-2, with the most preferred embodiment utilizing a mixture of TGF-β and IL-10.

The suppressive composition is incubated with the donor cells and a population of irradiated PMBC recipient cells (harvested as outlined above). The recipient cells are irradiated so that they cannot attack the donor cells, but will stimulate the donor cells to become tolerant to the recipient cells. The incubation occurs for a period of time sufficient to cause an effect, generally from 4 hours to 96 hours, although both shorter and longer time periods are possible.

In one embodiment, treatment of the donor cells with the suppressive composition is followed by immediate transplantation into the recipient patient, generally after the cells have been washed to remove the suppressive composition.

In a preferred embodiment, a second step is done. In this embodiment, after the donor cells have been conditioned or treated with the suppressive composition, they may be frozen or otherwise stored. Then a second step comprising obtaining a population of donor hematopoietic stem cells from aspirated bone marrow or PBMCs. Stem cells comprise a very small percentage of the white blood cells in blood, and are isolated as is known in the art, for example as described in U.S. Pat. Nos. 5,635,387 and 4,865,204, both of which are incorporated by reference in their entirety, or harvested using commercial systems such as those sold by Nexell. As outlined above, CD34+ stem cells can be concentrated using affinity columns; the eluted cells are a mixture of CD34+ stem cells and lymphocytes. The contaminating lymphocytes are generally be removed using known techniques such as staining with monoclonal antibodies and removal using conventional negative selection procedures.

Once the CD34+ stem cells have been isolated, they may be mixed with the donor cells previously treated with the suppressive composition and immediated introduced into the recipient patient.

In one embodiment, the cells are treated for a period of time, washed to remove the suppressive composition, and may additionally reincubated. The cells are preferably washed as outlined herein to remove the suppressive composition. Further incubations for testing or evaluation may also be done, ranging in time from a few hours to several days. If evaluation of any cellular characteristics prior to introduction to a patient is desirable, the cells may be incubated for several days to several weeks to expand numbers of suppressor cells.

Once the cells have been treated, they may be evaluated or tested prior to transplantation into the patient. For example, a sample may be removed to do: sterility testing; gram staining, microbiological studies; LAL studies; mycoplasma studies; flow cytometry to identify cell types; functional studies, etc. Similarly, these and other lymphocyte studies may be done both before and after treatment. A preferred analysis is a test using labeled recipient cells; incubating the treated tolerant donor cells with a labeled population of the recipient cells will verify that the donor cells are tolerant and won't kill the recipient cells.

In a preferred embodiment, the treatment results in the conditioning of the T cells to become non-responsive to histocompatibility antigens of the recipient so that GVHD is prevented.

In a preferred embodiment, prior to transplantation, the amount of total or active TGF-β can also be tested. As noted herein, TGF-β is made as a latent precursor that is activated post-translationally.

After the cell treatment, the donor cells are transplanted into the recipient patient. The MHC class I and class II profiles of both the donor and the recipient are determined. Preferably, a non-related donor is found that preferably matches the recipients HLA antigens, but may mismatch at one or more loci if a matched donor cannot be identified. The recipient patient has generally undergone bone marrow ablation, such as a high dose chemotherapy treatment, with or without total body irradiation.

The donor cells are transplanted into the recipient patient. This is generally done as is known in the art, and usually comprises injecting or introducing the treated cells into the patient as will be appreciated by those in the art. This may be done via intravascular administration, including intravenous or intraarterial administration, intraperitoneal administration, etc. For example, the cells may be placed in a 50 mol Fenwall infusion bag by injection using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

After reintroducing the cells into the patient, the effect of the treatment may be evaluated, if desired, as is generally outlined above and known in the art.

The treatment may be repeated as needed or required. After a period of time, the leukemic cells may reappear. Because the donor lymphocytes are now tolerant to the recipient's cells, the patient now receives a transfusion of unconditioned donor lymphocytes which recognize the leukemic cells as foreign and kill these cells.

In a preferred embodiment, the invention further provides kits for the practice of the methods of the invention, i.e., the incubation of the cells with the suppressive compositions. The kit may have a number of components. The kit comprises a cell treatment container that is adapted to receive cells from a donor. The container should be sterile. In some embodiments, the cell treatment container is used for collection of the cells, for example it is adaptable to be hooked up to a leukophoresis machine using an inlet port. In other embodiments, a separate cell collection container may be used.

The form and composition of the cell treatment container may vary, as will be appreciated by those in the art. Generally, the container may be in a number of different forms, including a flexible bag, similar to an IV bag, or a rigid container similar to a cell culture vessel. It may be configured to allow stirring. Generally, the composition of the container will be any suitable, biologically inert material, such as glass or plastic, including polypropylene, polyethylene, etc. The cell treatment container may have one or more inlet or outlet ports, for the introduction or removal of cells, reagents, suppressive compositions, etc. For example, the container may comprise a sampling port for the removal of a fraction of the cells for analysis prior to introduction into the recipient patient. Similarly, the container may comprise an exit port to allow introduction of the cells into the recipient patient; for example, the container may comprise an adapter for attachment to an IV setup.

The kit further comprises at least one dose of a suppressive composition. "Dose" in this context means an amount of the suppressive composition such as cytokines, that is sufficient to cause an effect. In some cases, multiple doses may be included. In one embodiment, the dose may be added to the cell treatment container using a port; alternatively, in a preferred embodiment, the dose is already present in the cell treatment container. In a preferred embodiment, the dose is in a lyophilized form for stability, that can be reconstituted using the cell media, or other reagents.

In some embodiments, the kit may additionally comprise at least one reagent, including buffers, salts, media, proteins, drugs, etc. For example, mitogens can be included.

In some embodiments, the kit may additional comprise written instructions for using the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Donor Lymphocyte ex vivo Treatment to Prevent an Immune Attack Against Blood Cells from an Unrelated Recipient A blood sample from a donor was obtained and lymphocytes prepared by density gradient centrifugation. T cells were prepared using a conventional negative selection procedure. These T cells were conditioned to prevent them from attacking the recipient cells. For this conditioning, the CD8+ T cells were mixed with irradiated stimulator cells from the recipient. The stimulator cells were derived from T cell-depleted blood cells from the recipient. The mixture of donor T cells and recipient stimulator cells were cultured for 48 hours with different concentrations of one or more cytokines. In this example the cytokines were TGF-β and IL-10. This procedure abolished the potential of the donor T cells to kill recipient cells, in FIG. 4B.

To test the ability of the donor T cells to recognize and kill recipient blood cells, the donor T cells were cultured with irradiated stimulator cells for 5 days. Then the donor cells were cultured for 4 hours with a sample of recipient radio-labeled blood cells. When the recipient's cells are killed they release radioisotope into the culture medium. By determining the amount of radioisotope released, one can calculate the percentage of cells killed. In the standard cytotoxicity assay shown in FIG. 1, donor cells were cultured with labeled recipient cells in 30 to 1, 15 to 1, and 7.5 to 1 ratios. These combinations of donor and recipient cells are called effector to target ratios. Killing is indicated by the various symbols. As expected, maximum killing was seen at the highest effector to target cell ratio. In panel A, the open circles shows that if 30 donor cells were mixed with 1 recipient cell, 40 percent of the recipient cells were killed. When donor T cells were conditioned with very small concentrations of TGF-β(0.01 or 0.1 nanograms per ml), they had no effect on killing. However, if the T cells were treated with 1 nanogram per ml of TGF-β, the killing of recipient cells decreased by 50 percent. Panel B shows that if the T cells were treated with IL-10, killing also decreased by 50%. If the T cells had been conditioned with both IL-10 and TGF-β at 1 nanogram per ml, these cells completed blocked the killing of recipient cells; killing was almost undetectable. Various combinations of mitogens, cytokines, and monoclonal antibodies can be used to make T cells non-responsive.

Example 2

CD8+ T Cells from the Donor Conditioned ex vivo to Prevent other Donors T Cells from Mounting an Attack Against Blood Cells from an Unrelated Recipient A blood sample from a donor was obtained and lymphocites prepared. CD8+ T cells were mixed with irradiated stimulator cells of the recipient and either TGF-β(picograms per ml) or IL-12 100 U/ml. IL-12 is known to enhance the ability of CD8+ T cells to develop the capacity to kill. Here IL-12 was used to show that a given population of CD8+ cells can be induced to kill or to block killing depending upon how they are activated. Other CD8 + cells were cultured in culture medium only as a control (CD8med).

The CD8+ T cells, the stimulator cells and the cytokines were cultured for 48 hours and the cytokines were removed from the cultures by washing. This procedure not only abolished the potential of the TGF-β, conditioned CD8+ cells to kill the recipient cells, but also induced them to prevent other donor T cells from killing the recipient cells (FIG. 4C).

To enable the donor T cells to recognize and kill recipient blood cells, the donor cells were cultured with irradiated stimulator cells for five days. Then the donor cells were cultured for 4 hours with a sample of recipient radiolabeled blood cells. The open circles show the level of donor cells of recipient cells when no CD8+ cells were added. At a 30:1 effector to target cell ration, 30% of the recipient's cells were killed. If CD8+ cells that had been cultured for 48 hours without cytokines were added, there was no change in the killing (CD8+ +Med, solid circles). If the CD8+ cells had been conditioned with TGF-β, killing was suppressed by about 50%. However, the CD8+ T cells conditioned with TGF-β not only did not kill, but the decreased levels of cytotoxicity indicate that they blocked the ability of other T cells to kill blood cells of the recipient.

Example 3

Treating a Patient with Chronic Myelocytic Leukemia with the Stem Cells from a Histoincompatible Donor: Tolerization with Mitogens The harvested PBMC of the donor are placed in a sterile container in HBBS as in Example 1. The cells are then incubated with mitogens to induce lymphocytes to become non-responsive to histocompatibility antigens of the recipient. In this case the cells are incubated with physiological concentrations of concanavalin A (Con A) for 4 to 72 hours using standard incubation techniques. The concentration of Con A used can range from about 0.01 to about 10 micrograms/ml with 1 microgram/ml being presently preferred. Alternatively, SEB may be used as the mitogen at concentrations of 0.001 to 100 ng/ml.

The incubation of the mononuclear cells in the mitogen solution increases the population of T suppressor cells. These cells, when transferred to the recipient, will enable the stem cells to engraft without causing GVHD. Although it is not known how the mitogens work, it is believed to induce the production of TGF-beta by certain mononuclear cells in preparation, and the TGF-beta acts on T cells to become suppressor cells.

After the cells have been incubated with the mitogens, the cells are washed with HBBS to remove any mitogens that are in the solution. The cells are suspended in 200–500 ml of HBBS, mixed with the stem cells and administered to a patient with CML who has been treated with myeloablative agents to prepare the stem cells for engraftment.

Once the donor hematopoietic cells lymphocites engraft in the recipient, and the patient again becomes healthy and free of leukemic cells. If the leukemic cells recur, the patient receives a transfusion of donor lymphocites and the leukemic cells again disappear.

Example 4

Treating a Patient with Chronic Myelocytic Leukemia with the Stem Cells from a Histoincompatible Donor: Tolerization with Anti-CD2 Monoclonal Antibodies The harvested enriched stem cell preparation of the donor are placed in a sterile container in HBBS as in Example 1. The cells are then incubated with anti-CD2 monoclonal antibodies to induce lymphocytes to become non-responsive to histocompatibility antigens of the recipient. In this case, the cells are incubated with anti-CD2 monoclonal antibodies for 4 to 72 hours using standard incubation techniques. The concentration of anti-CD2 monoclonal antibodies are 10 ng/ml to 10 ug/ml. Optionally, 1–1000 units of IL-2 can be added.

The incubation of the mononuclear cells in the anti-CD2 solution increases the population of T suppressor cells. These cells, when transferred to the recipient will enable the stem cells to engraft without causing GVHD. It is believed that incubation with anti-CD2 monoclonal antibodies induces the production of TGF-beta by certain monuclear cells in preparation, and the TGF-beta acts on T cells to become suppressor cells.

After the cells have been incubated with the anti-CD2 monoclonal antibodies, the cells are washed with HBBS to remove antibodies that are in the solution. The cells are suspended in 200–500 ml of HBBS mixed with the stem cells harvested previously and administered to a patient with CML who has been treated with myeloblative agents to prepare the stem cells for engraftment.

Once the donor hematopoietic cells lymphocytes engraft in the recipient, and the patient again becomes healthy and free of leukemic cells. If the leukemic cells recur, the patient receives a transfusion of donor lymphocytes and the leukemic cells again disappear.

Example 5

Treating a Patient with Chronic Myelocytic Leukemia with the Stem Cells from a Histoincompatible Donor: Tolerization with Mitogens and Cytokines The harvested PBMC of the donor are placed in a sterile container HBBS as in Example 1. The cells are then incubated with cytokines and mitogens to induce lymphocytes to become non-responsive to histocompatibility antigens of the recipient. In this case the cells are incubated with physiological concentrations of Con A or SEB, IL-2 or IL-10 and TGF-beta for 4 to 72 hours using standard incubation techniques.

After the cells have been incubated with the cytokines and mitogens, the cells are washed with HBBS to remove any cytokine and mitogen that are in the solution. The cells are suspended in 200–500 ml of HBBS mixed with the stem cells and administered to a patient with CML who has been treated with myeloabative agents to prepare the stem cells for engraftment.

Once the donor hematopoietic cells and lymphocytes engraft in recipient and the patient again becomes healthy and free of leukemic cells. If the leukemic cells recur, the patient receives a transfusion of donor lymphocytes and the leukemic cells again disappear.

Example 6

Treating a Patient with Chronic Myelocytic Leukemia with the Stem Cells from a Histoincompatible Donor; Tolerization with a Mitogen and Cytokine The harvested PBMC of the donor are placed in a sterile container in HBBS as in Example 1. The cells are then incubated with a cytokine and a mitogen to induce lymphocytes to become non-responsive to histocompatibility antigens of the recipient. In this case the cells are incubated with physiological concentrations of ConA, and IL-2 for 4 to 72 hours using standard incubation techniques. In another case, SEB could be used.

After the cells have been incubated with the cytokines and mitogens, the cells are washed with HBBS to remove any cytokine and mitogen that are in the solution. The cells are suspended in 200–500 ml of HBBS mixed with stem cells and administered to a patient with CML who has been treated with myeloablative agents to prepare the stem cells for engraftment.

Example 7

Treating a Patient with Chronic Myelocytic Leukemia who has Developed GVHD Following the Stem Cell Transplant In the instance that the initial procedure to prevent early or late GVHD following the stem cell transplant is not successful, this event will be managed BY transfer of a larger number of donor T cells that have been conditioned to become suppressor cells. Approximately $1\times10^9$ PBMCs obtained by leukopheresis are concentrated in a sterile leukopak; in Hanks balanced salt solution (HBBS). The PMMCs or separated CD8+ T cells (or the specific suppressor cell precursor subset CD8+CD45RA+C27+) prepared by immunoaffinity columns will be treated with antiCD2 monoclonal antibodies and/or mitogens and/or cytokines described above to condition them to become suppressor cells.

After incubation with the cytokines or mitogens for a period of time ranging from 4 hours to 72 hours, the cells are washed to remove the cytokines or mitogens and then are transferred to the recipient. These conditioned T cells migrate to lymphoid organs and suppress the GVHD.

Besides chronic myelocytic leukemia, other hematologic malignancies such as acute and chronic leukemias, lymphomas, solid tumors such as breast carcinoma or renal cell carcinoma among a few, and non-malignant diseases such as severe anemias (thalassemia, sickle cell anemia) can be treated with mismatched allogeneic stem cells.

Another aspect of this invention is a kit to perform the cell incubation with the cytokines. The kit comprises a sterile incubating container with the appropriate concentration of cytokines preloaded within the container. In one embodiment of the kit, the cytokines are present in lyophilized form in the container. The container is preferably a bag, similar to an IV bag. The lyophilized cytokines are reconstituted with HBBS and then the cells are injected into the container and thoroughly mixed and incubated. In another embodiment of the invention the cytokines are already in solution within the container and all that has to be done is the injection of washed stem cell preparation and incubation.

What is claimed is:

1. A method for treating donor cells to ameliorate graft versus host disease in a recipient patient comprising:
    a) removing peripheral blood mononuclear cells (PBMC) from a donor;
    b) treating said cells with a suppressive composition comprising TGF-β for a time sufficient to induce T cell tolerance; and
    c) administering said cells to said patient.

2. A method according to claim 1 wherein said suppressive composition firther comprises IL-10.

3. A method according to claim 1 wherein said method further comprises adding said cells to donor stem cells prior to administering to said patient.

4. A method according to claim 1 wherein said suppressive composition firther comprises IL-2.

* * * * *